United States Patent [19]

Peyman

[11] Patent Number: 4,729,373
[45] Date of Patent: Mar. 8, 1988

[54] LASER-POWERED SURGICAL DEVICE WITH A VIBRATING CRYSTALLINE TIP

[76] Inventor: Gholam, A. Peyman, 535 N. Michigan Ave., Apt. 3001, Chicago, Ill. 60611

[21] Appl. No.: 943,065

[22] Filed: Dec. 18, 1986

[51] Int. Cl.$^4$ .............................................. A61B 17/36
[52] U.S. Cl. .................... 128/303.1; 604/22
[58] Field of Search .................... 128/303.1, 395–398, 128/24 A; 604/22

[56] References Cited

U.S. PATENT DOCUMENTS

| | | | |
|---|---|---|---|
| 4,233,493 | 11/1980 | Nath | 128/303.1 |
| 4,478,217 | 10/1984 | Shimada et al. | 128/303.1 |
| 4,539,987 | 9/1985 | Nath et al. | 128/303.1 |

*Primary Examiner*—Lee S. Cohen
*Attorney, Agent, or Firm*—Roylance, Abrams, Berdo & Goodman

[57] ABSTRACT

A laser-powered surgical device with a vibrating crystalline tip for directly engaging the tissue to be treated. The device comprises a hollow handle, a laser energy transmitting conduit received in the handle and having first and second ends extending out of the handle, the first end engaging the tissue to be treated and the second end coupled to a laser energy generator, and a vibration assembly for vibrating the conduit's first end relative to the handle. The vibration assembly is driven mechanically or ultrasonically. The conduit's first end comprises the crystalline tip which is formed of sapphire, glass, quartz or ruby.

16 Claims, 6 Drawing Figures

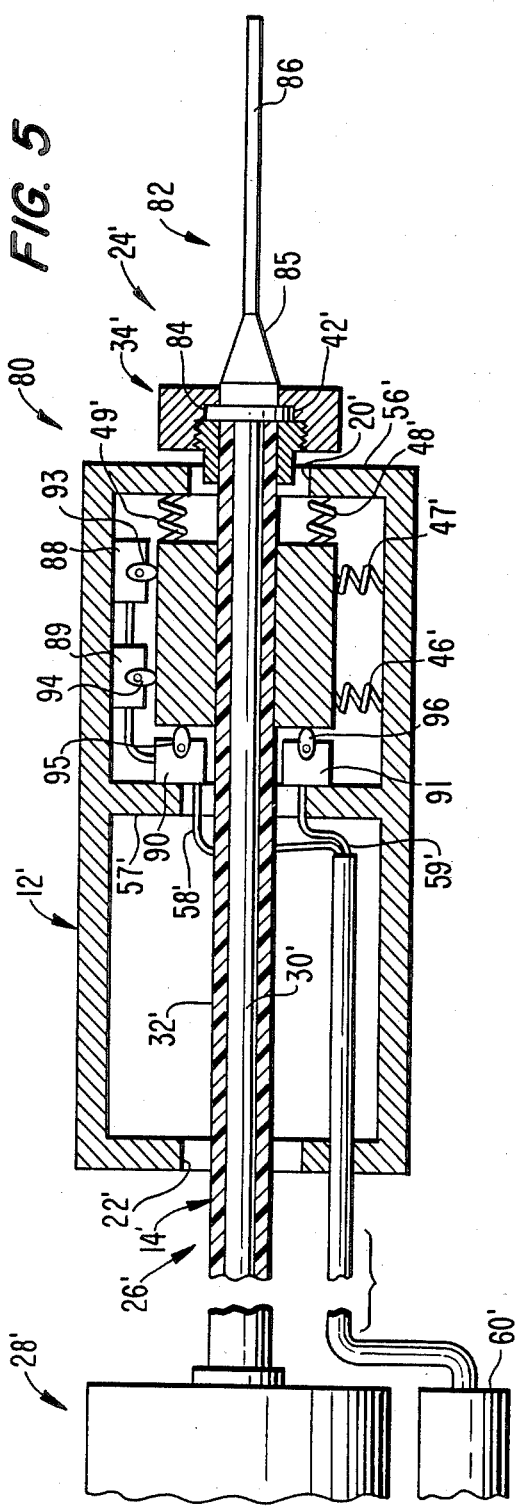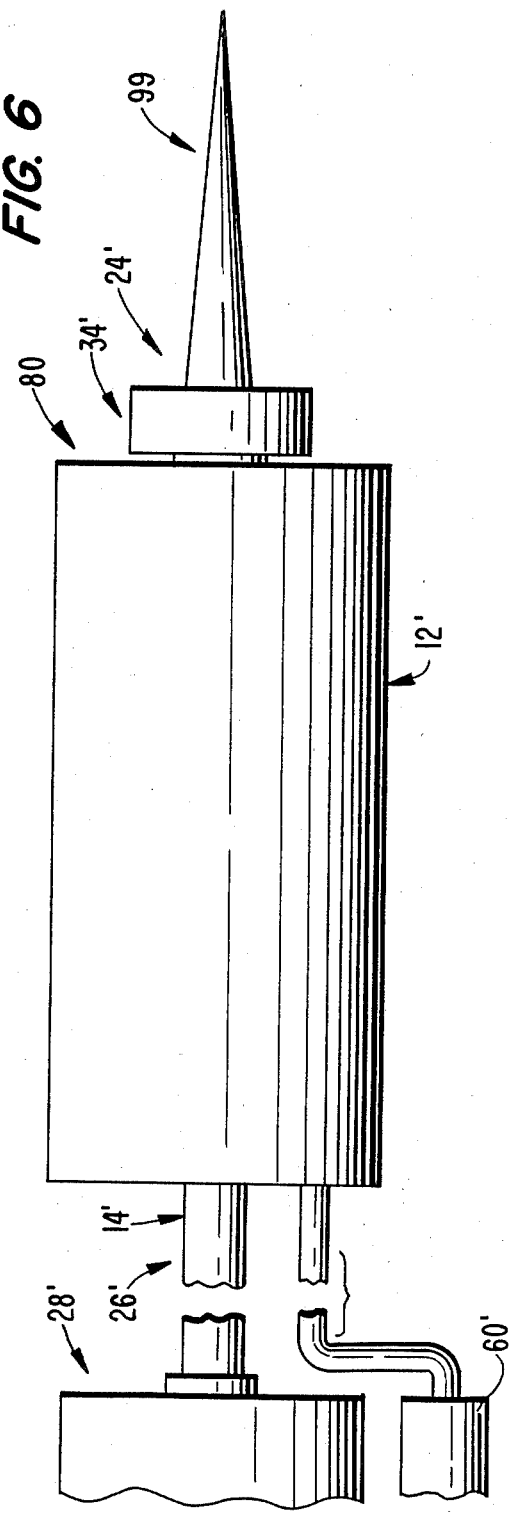

LASER-POWERED SURGICAL DEVICE WITH A VIBRATING CRYSTALLINE TIP

FIELD OF THE INVENTION

The invention relates to surgical devices, and more particularly to a laser-powered surgical device with a vibrating crystalline tip for directly engaging the tissue to be treated.

BACKGROUND OF THE INVENTION

Lasers have been used extensively to perform surgery, especially on the eye. The surgical devices utilizing laser power are basically divided into two types, non-contact and contact.

In the non-contact type, laser light transmission systems typically use a flexible quartz fiber in combination with a neodymium: YAG laser or an argon laser, or a mirror reflection system in combination with a carbon dioxide laser. Since these light transmission systems are non-contact systems, they have distinct disadvantages including inaccurate beam orientation, damage to the quartz tip should it come into contact with tissue or blood, and the lack of the surgeon's typical "touch technique".

Of the contact type of laser-powered surgical devices, one comprises an artifical sapphire probe connected to a quartz fiber for use with an Nd:YAG laser. In this device, the tip of the sapphire probe engages the tissue to be treated. The treatment comprises photocoagulation, cutting, or tissue vaporization, which is also known as ablation. In this device, the sapphire probe is coupled via a connector to the end of the quartz fiber which in turn is connected to the laser.

While the sapphire probe contact system is advantageous in providing accuracy and a touch technique, it does have significant disadvantages. First, tissue tends to adhere to the sapphire probe, thereby tending to damage adjacent tissue structures when the probe is moved. Secondly, the sapphire probe tends to provide too much coagulation of the tissue due to heat, thereby scarring and opacifying, for example, ocular tissue.

Accordingly, there is still a strong and continuing need for improvement in constructing laser-powered devices for surgery.

SUMMARY OF THE INVENTION

Thus, a primary object of this invention is to provide a laser-powered surgical device which can treat tissue by direct engagement while preventing adhesion and excess coagulation.

Another object of the invention is to provide a laser-powered surgical device with a vibrating crystalline tip that can deliver laser energy directly to tissue and also fragment the tissue via the vibration.

Another object of the invention is to provide a laser-powered surgical device that utilizes direct contact with the tissue to be treated and thereby provides a touch or feel for the surgeon.

A further object of the invention is to provide a laser-powered surgical device with various types of tips to perform different types of surgical treatment.

The foregoing objects are basically attained by providing a surgical device adapted to be connected to a laser energy generator, the combination comprising: a hollow handle having first and second open ends; a laser energy transmitting conduit received in the hollow housing, the conduit having a first end extending from the handle throughg the first topen end an adapted to engage tissue to be treated, and a secondend extending from the handle through the second open end and adapted to be connected to a laser energy generator; and a vibration assembly, coupled to the handle and the conduit, for vibrating the conduit first end relative to the handle.

Other objects, advantages and salient features of the invention will become apparent from the following detailed description, which, taken in conjunction with the annexed drawings, discloses preferred embodiments of the invention.

DRAWINGS

Referring now to the drawings which form a part of this original disclosure:

Figure 1:
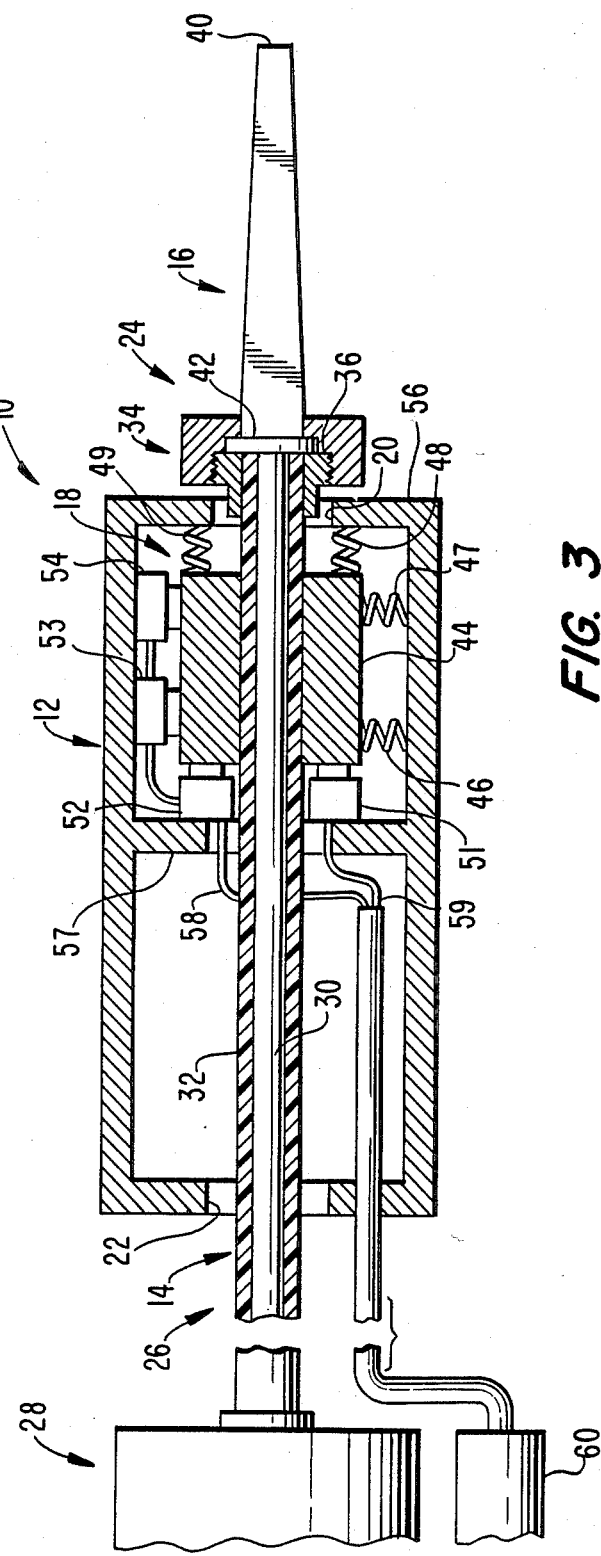
FIG. 1 is a top plan view in longitudinal section showing the laser-powered surgical device in accordance with the invention where the vibration is provided by ultrasonic transducers.

FIG. 5 is a top plan view in longitudinal section of a modified laser-powered surgical device in accordance with the invention, this embodiment being similar to that shown in FIG. 1, except that the vibration assembly is formed from a plurality of motors and rotating cams and the crystalline tip has a substantially cylindrical end; and FIG. 6 is a top plan view of the laser-powered surgical device shown being conical and pointed.

DETAILED DESCRIPTION OF THE INVENTION

Figure 2:
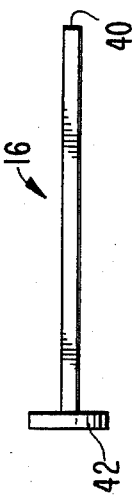
FIG. 2 is a side elevational view of the crystalline tip shown in FIG. 1 and having a substantially rectangular cross section and a flat distal end.

Referring now to FIGS. 1 and 2, the laser-powered surgical device 10 in accordance with the invention comprises a hollow handle 12, a laser energy transmitting conduit 14 including a crystalline tip 16, and a vibration assembly 18 for vibrating the crystalline tip relative to the handle. The device is particularly suited for ocular surgery to modify the curvature of the cornea, although it can be used on internal tissue in, for example, the brain, kidneys or intestines.

Handle 12 is hollow and tubular wih a straight longitudinal axis along which the conduit 14 extends as seen in FIG. 1. The handle can be made of any suitable material such as metal or plastic. The handle has a first open end 20 and a second open end 22 along the longitudinal axis.

The laser energy transmitting conduit 14 has a first end 24 and a second end 26, the first end 24 extending from the handle through the first open end 20 and the second end 26 extending from the handle through the second open end 22. This second end is connected to a laser energy generator 28. Advantageously, the generator is of the Nd:YAG type, and is capable of producing 20 watts of power including eight watts at the end of the conduit 14. The preferable wavelength of the laser energy is 1.06μ.

The laser energy transmitting conduit 14 comprises an optical fiber 30, preferably quartz, of approximately 500μ in diameter, a conventional plastic sheath 32 covering the fiber, a connector 34, and the crystalline tip 16. The adjacent ends of the fiber and the tip shown in FIG. 1 abut one another to provide a continuous path therealong for the laser energy. If necessary, a cooling agent, such as carbon dioxide gas, can be directed to the end of the fiber to prevent melting of the fiber.

The connector 34 comprises a sleeve 36 rigidly coupled, such as by adhesive, to the end of sheath 32 and having external threads, and a bushing 38 having internal threads for threadedly engaging the sleeve 36, with the crystalline tip 16 rigidly coupled therebetween as seen in FIG. 1.

The crystalline tip 16 is advantageously formed from an artifical sapphire or it could also be made of glass, quartz, or ruby. Preferably, the crystal has as few air bubbles therein as possible in order to avoid refraction of the laser energy. The crystalline tip 16 advantageously has a thickness at the distal end of about 0.2 mm.

As seen in FIGS. 1 an 2, the tip 16 in top plan view tapers towards the flat distal end 40 and is substantially rectangular in cross section with a disk-shaped flange 42 at the other end and rigidly received in the connector 34. The flat distal end can be used as a knife to cut or scrape tissue.

As seen in FIG. 1, located inside the handle 12 is the vibration assembly 18 which comprises a ring 44, four coiled springs 46–49, and four ultrasonic transducers 51–54. Ring 44 is preferably formed from metal and has the conduit 14 received therein and rigidly coupled thereto, such as by adhesive. The coiled springs 46 and 47 are laterally oriented and engage the inner lateral surface of the handle and the outer lateral surface of the ring. Coiled springs 48 and 49 engage the inner axially-facing surface of the end wall 56 of the handle and the outer axially-facing surface of an end of the ring. Similarly, ultrasonic transducers 51 and 52 engage a central wall 57 inside the handle, are suitably rigidly coupled thereto, and engage the outer axially-facing surface of the end of the ring opposite from the springs 48 and 49. Ultrasonic transducers 53 and 54 are suitably rigidly coupled to the inside lateral surface of the handle and engage the outer lateral surface of the ring opposite the coiled springs 46 and 47. If necessary, additional springs can be used to support the ring so as to allow it to vibrate or any other suitable cushioned support can be used.

Suitable electrical conductors 58 and 59 are connected to the ultrasonic transducers and to a suitable power source 60.

Thus, by actuating ultrasonic transducers 51 and 52, the ring 44 can be oscillated axially of the handle against the action of springs 48 and 49. By actuating ultrasonic transducers 53 and 54, the ring can be oscillated against springs 46 and 47 laterally of the longitudinal axis of the handle. Advantageously, the frequency of the oscillation is 6,000 times per minute or even up to a million a minute.

Since the crystalline tip 40 is rigidly coupled via the connector 34 to optical fiber 30 and sheath 32, and the sheath is in turn rigidly coupled to the ring, the vibration of the ring via the transducers will in turn vibrate the tip as desired. A preferred amplitude of the various oscillations is about 0.1 mm.

As shown in FIG. 1, the first open end 20 of the handle is larger than the outer diameter of the sheath 32 and sleeve 36; thus, there is adequate room for lateral vibration of the conduit relative to the housing. Since the amplitude of 0.1 mm is rather small, the axial oscillation can be accepted due to slack in the conduit 14. If necessary, an extra loop of the conduit can be made to accept this amplitude and placed inside the handle if desired.

In utilizing the laser powered surgical device 10, the distal end 40 of the tip directly engages the tissue to be treated, and tends to photocoagulate, cut, or vaporize any tissue it is in contact with due to the laser energy transmitted from the laser energy generator, along the optical fiber 30 and through the crystalline tip 16. In addition, the vibration provided to the tip avoids adhesion or excess coagulation and also provides the device with the ability to fragment tissue it engages due to the vibration. In this regard, it is contemplated that the device can be used with just the laser power on, just the vibration on, or both in combination. Likewise, the lateral and axial oscillations can take place independently, alternately or together.

FIGS. 3 AND 4

Figure 3:
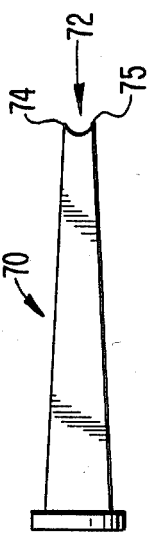
FIG. 3 is a top plan view of a modified crystalline tip which is similar to the tip shown in FIGS. 1 and 2, except that it has a curved distal end.
Figure 4:
FIG. 4 is a side elevational view of the crystalline tip shown in FIG. 3.

As seen in FIGS. 3 and 4, a modified crystalline tip 70 is shown, this tip capable of being used with the device 10 shown in FIG. 1. The tip 70 is substantially the same as that shown in FIGS. 1 and 2, except the distal end 72 is curved inwardly and defines a pair of points 74 and 75 at the ends of the curve. This curved end is advantageous in shaving a thickness from a cornea to modify corneal curvature.

FIG. 5

As seen in FIG. 5, a modified surgical device 80 is shown which is the same as device 10 shown in FIG. 1, except that the vibration assembly and tip configuration are modified. Where the parts are the same as shown in FIGS. 1 and 5, the same reference numerals are used with the addition of a prime.

Thus, in FIG. 5, the crystalline tip 82 has, in addition to the disk-shaped flange 42', a cylindrical base 84, a frustoconical section 85, and a cylindrical distal end 86. Advantageously the diameter of the cylinder can be from 0.05 to 2.00 mm in diameter. This cylindrical end is useful in puncturing or boring holes in tissue, such as during treatment for glaucoma.

The other modification is the use of motors 88–91 and eccentric cams 93–96 respectively coupled to rotating shafts on the motors, these cams engaging the outer surfaces of the ring 44' as seen in FIG. 5. Upon rotation of cams 95 and 96, ring 44' is oscillated axially of the handle and upon rotation of cams 93 and 94, ring 44' is oscillated laterally of the handle.

The motors 88–91 are supported like the transducers in FIG. 1, and can be any suitable type of miniature motors including electrical, pneumatic, or hydraulic. They are connected to a suitable power source 60' via conductors 58' and 59' and provide the same frequency and amplitude as use of the ultrasonic transducers discussed above.

FIG. 6

In FIG. 6, device 80 is once again shown, except that the crystalline tip is modified and is in the form of a frustoconical or conical tip 99, which is useful for forming holes in the tissue.

While advantagous embodiments have been chosen to illustrate the invention, it will be understood by those skilled in the art that various changes and modifications can be made therein without departing from the scope of the invention as defined in the appended claims.

What is claimed is:

1. A surgical device adapted to be connected to a laser energy generator, the combination comprising:
   a hollow handle having first and second open ends;
   a laser energy transmitting conduit received in said hollow handle,
   said conduit having a first end extending from said handle through said first open end and adapted to engage tissue to be treated, and a second end extending from said handle through said second open end and adapted to be connected to a laser energy generator; and
   means, coupled to said handle and said conduit, for vibrating said conduit first end relative to said handle.

2. A device according to claim 1, wherein said handle has a longitudinal axis, and same means for vibrating includes means for oscillating said first end laterally of said longitudinal axis.

3. A device according to claim 2, wherein said means for vibrating further includes means for oscillating said first end axially of said longitudinal axis.

4. A device according to claim 1, wherein said handle has a longitudinal axis, and said means for vibraing includes means for oscillating said first end axially of said longitudinal axis.

5. A device according to claim 1, wherein said means for vibrating includes a cam and means for rotating said cam.

6. A device according to claim 1, wherein said means for vibrating includes an ultrasonic transducer.

7. A device according to claim 1, wherein said laser energy transmitting conduit comprises an optical fiber.

8. A device according to claim 7, wherein said laser energy transmitting conduit first end comprises a crystal and means for coupling said crystal to said optical fiber.

9. A device according to claim 1, wherein said laser energy transmitting conduit first end comprises a crystal.

10. A device according to claim 9, wherein said crystal is formed from a material selected from the group consisting of sapphire, glass, quartz and ruby.

11. A device according to claim 9, wherein said crystal has a distal end which is flat.

12. A device according to claim 9, wherein said crystal has a distal end which is curved.

13. A device according to claim 9, wherein said crystal has a distal end which is pointed.

14. A device according to claim 9, wherein said crystal has a distal end, and said crystal tapers inwardly towards said distal end thereof.

15. A device according to claim 9, wherein said crystal has a distal end which is substantially cylindrical.

16. A device according to claim 9, wherein said crystal has a substantially rectangular cross section.

* * * * *